US006372213B2

(12) United States Patent
Um et al.

(10) Patent No.: US 6,372,213 B2
(45) **Date of Patent: *Apr. 16, 2002**

(54) METHOD OF TREATING SICKLE CELL DISEASE OR THALASSEMIA

(75) Inventors: Suzane Lee Um, Indianapolis; Barbara Gail Utterback, Avon; Sau-Chi Betty Yan, Indianapolis, all of IN (US)

(73) Assignee: Eli Lilly and Company, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/444,746

(22) Filed: Nov. 22, 1999

Related U.S. Application Data

(60) Provisional application No. 60/109,474, filed on Nov. 23, 1998.

(51) Int. Cl.[7] .................... A61K 38/48; A61K 38/00; C12N 9/64

(52) U.S. Cl. .................... 424/94.64; 424/94.64; 435/226; 514/2

(58) Field of Search .................... 435/226; 514/2; 424/94.64

(56) References Cited

U.S. PATENT DOCUMENTS

| | | | | |
|---|---|---|---|---|
| 4,775,624 A | | 10/1988 | Bang et al. | 435/226 |
| 4,981,952 A | | 1/1991 | Yan | 530/384 |
| 4,992,373 A | | 2/1991 | Bang et al. | 435/226 |
| 5,453,373 A | | 9/1995 | Gerlitz et al. | 435/240.2 |
| 5,478,558 A | | 12/1995 | Eibl et al. | 424/94.63 |
| 5,516,650 A | | 5/1996 | Foster et al. | 435/68.1 |
| 5,550,036 A | | 8/1996 | Grinnell | 435/69.1 |
| 6,008,199 A | * | 12/1999 | Grinnell et al. | 514/21 |

FOREIGN PATENT DOCUMENTS

| | | |
|---|---|---|
| EP | 0 318 201 | 11/1988 |
| EP | 0 357 296 | 8/1989 |
| EP | 0357296 A1 * | 3/1990 |
| EP | 0 445 939 | 9/1991 |
| EP | 0318201 B1 * | 3/1996 |
| WO | WO 97/20043 | 6/1997 |

OTHER PUBLICATIONS

Nsiri, B., et al., 1996, "Abnormalities of coagulation and fibrinolysis in homozygous sickle cell disease", Hematology and Cell Therapy, vol. 38, pp. 279–284.*

Wright, J. G., et al., 1997, "Activated protein C resistance in homozygous sickle cell disease", British Journal of Haematology, vol. 96, pp. 854–856.*

Wright, J. G., et al., 1997, "Protein C and protein S in homozygous sickle cell disease: does hepatic dysfunction contribute to low levels", British Journal of Haematology, vol. 98, pp. 627–631.*

Giordano, P., et al., 1997, "Resistance to activated protein C as a risk factor of stroke in a thalassemic patient", Haematologica, vol. 82, pp. 698–700.*

Giordano, P., et al., 1998, "Resistance to activated protein C in thalassemic patients: an underlying cause of thrombosis", European Journal of Haematology, vol. 61, pp. 123–127.*

Westerman, M. P., et al., 1998, "Antiphospholipid antibodies, proteins C and S and clotting changes in sickle cell disease", Blood, vol. 92, No. 10, Supplement 1, Abstract No. 169, at p. 43a.*

Margaing–Koka, et al., "Decreased Protein S Activity in Sickle Cell Disease", *Nouv Rev Fr Hamatol* (1993) 35: 425–430.

Ampaiwan Chuansumrit, M.D., et al., "Thrombotic Risk of Children with Thalassemia", *J Med Assoc Thai* 76(2): 80–84, 1993.

M. Peters, et al., Enhanced Thrombin Generation in Children with Sickle Cell Disease, *Thrombosis and Haemostasis*, 71(2): 69–172, 1994.

David A. Tam, MD, "Protein C and Protein S Activity in Sickle Cell Disease andStroke", *Journal of Child Neurology*, 12(1): 19–21, 1997.

Karayalcin, et al., *The American Journal of Pediatric Hematology/Oncology* 11(3): 320–323, 1989.

Mohsen A.F. El–Hazmi, et al., Blood Proteins C and S in Sickle Cell Disease, *Acta Haematol* 90:114–119, 1993.

Akira Shirahata, et al., Protein C and Protein S Deficiency in Thalassemic Patients, *Southeast Asian J Trop Med Pub Health* 23(2): 65–73, 1992.

David Green, et al., "Is Sickle Cell Crisis a Thrombotic Event?", *American Journal of Hematology* 23:317–321, 1986.

Peter C. Ferrera, M.D., et al., Etiology of Pediatric Ischemic Stroke, *American Journal of Emergency Medicine* 15(7): 671–679, 1997.

Grinnell, et al., "Trans–Activated Expression of Fully Gamma–Carboxylated Recombinant Human Protein C, An Antithrombotic Factor", *Bio/Technology* 5:1189–1192, 1987.

* cited by examiner

*Primary Examiner*—Ponnathapu Achutamurthy
*Assistant Examiner*—William W. Moore
(74) *Attorney, Agent, or Firm*—Brian P. Barrett

(57) ABSTRACT

The present invention provides a method of treatment of sickle cell disease (SCD) or thalassemia with protein C. The claimed invention provides a needed therapy for potentially serious and debilitating disorders while avoiding complications such as bleeding tendency, toxicity and general side effects of currently available anti-coagulant agents.

7 Claims, No Drawings

METHOD OF TREATING SICKLE CELL DISEASE OR THALASSEMIA

This application claims priority of Provisional Application Ser. No. 60/109,474 filed Nov. 23, 1998.

FIELD OF THE INVENTION

This invention relates to medical science particularly the treatment of sickle cell disease or thalassemia with protein C.

BACKGROUND OF THE INVENTION

Protein C is a vitamin K dependent serine protease and naturally occurring anticoagulant that plays a role in the regulation of hemostasis by inactivating Factors Va and VIIIa in the coagulation cascade. Human protein C circulates as a 2-chain zymogen, but functions at the endothelial and platelet surface following conversion to activated protein C (aPC) by limited proteolysis with thrombin in complex with the cell surface membrane protein, thrombomodulin.

In conjunction with other proteins, aPC functions as perhaps the most important down-regulator of blood coagulation resulting in protection against thrombosis. In addition to its anti-coagulation functions, aPC hasanti-inflammatory effects through its inhibition of cytokine generation (e.g. TNF and IL-1) and also exerts profibrinolytic properties that facilitate clot lysis. Thus, the protein C enzyme system represents a major physiological mechanism of anti-coagulation, anti-inflammation, and fibrinolysis.

Sickle cell diseases (SCD) and thalassemia are inherited hemoglobulinopathies characterized by a structural hemoglobin defect. SCD include diseases which cause sickling of the red blood cells, and includes sickle cell anemia (which results from rwo hemoglobulin S genes), sickle α-thalassemia (one hemoglobin S and one α-thalassemia gene), and hemoglobin SC disease (one hemoglobin S and one hemoglobin C), and the rarer disease, hemoglobin C Harlem. Thalassemia includes β-thalassemia and α-thalassemia. These hereditary diseases have significant morbidity and mortality and affect individuals of African American heritage, as well as those of Mediterranean, Middle Eastern, and South East Asian descent. These disease commonly cause severe pain in sufferers in part due to ischemia caused by the damaged red blood cells blocking free flow through the circulatory system.

SCD is considered a prethrombotic state, since certain characteristics of sickle cells such as abnormal adhesivity and absence of membrane phospholipid asymmetry are involved in the thrombotic process [Marfaing-Koka, et al., *Nouv Rev Fr Hamatol* 35:425–430, 1993]. Most of the morbidity of SCD appears to be related to the appearance of occlusion of the microvasculature, resulting in widespread ischemia and irreversible organ damage. In addition, pulmonary microthromboemboli have been described in 44 percent of autopsies from thalassemia patients [Chuansumrit et al., *J Med Assoc Thai,* 76(2):80–84, 1993].

Investigators employing sensitive assays for coagulation have documented signs of a hypercoagulable state resulting in vaso-occlusion in adults with SCD. Vaso-occlusion is a complex process involving cellular, vascular, and humoral factors and possibly thrombotic events. The occurrence of stroke is probably the most devastating complication of SCD in a child [Peters, et al., *Thrombosis and Haemostasis* 71(2): 69–172, 1994; Tam D., *Journal of Child Neurology* 12(1): 19–21, 1997].

Deficiencies of protein C and enhanced thrombin generation have been reported in patients with SCD or thalassemia [Karayalcin, et al., *The American Journal of Pediatric Hematology/Oncology* 11(3):320–323, 1989; Hazmi, et al., *Acta Haematol* 90:114–119, 1993; Peters, 1994]; Shirahata et al. *Southeast Asian J Trop Med Pub Health* 23(2):65–73] The lower protein C levels in SCD or thalassemia are either due to decreased production or increased consumption. Therefore, a coagulation imbalance exists in patients with SCD or thalassemia which in turn may be responsible for the adverse clinical effects observed in these patients.

Currently, there is no effective therapy to prevent the pain associated with SCD or thalassemia or to correct the disease causing genes. The current treatment approach includes intravenous solutions of glucose and electrolytes, narcotic analgesics, and antiinflammatory agents [Green et al. *American journal of Hematology* 23:317–321, 1986]. Recently, the chemotherapeutic agent hydroxyurea has been used in an increasing number of sickle cell anemia patients. In more severe cases or following ischemic stroke, exchange transfusions and bone marrow transplantation have been utilized [Ferrera et al. *American Journal of Emergency Medicine* 15(7):671–679, 1997]. Prophylactic transfusion is the only accepted therapy for patients with SCD that have had a stroke. Therefore, a need exists for a safe, effective therapy of patients with SCD or thalassemia.

The present invention is the first to describe the treatment of SCD or thalassemia with protein C. Protein C, with its anticoagulant, antiinflammatory, and profibrinolytic activities, is useful for the treatment of the hypercoagulable state or protein C deficiency that occurs in SCD or thalassemic patients.

SUMMARY OF THE INVENTION

The present invention provides a method of treating a patient suffering from sickle cell disease (SCD) or thalassemia which comprises, administering to said patient a pharmaceutically effective amount of protein C.

The present invention further provides a method of treating sickle cell disease or thalassemia in a patient in need thereof, which comprises administering to said patient a pharmaceutically effective amount of activated protein C such that an activated protein C plasma level of about 2 ng/ml to about 300 ng/ml is achieved.

DETAILED DESCRIPTION OF THE INVENTION

For purposes of the present invention, as disclosed and claimed herein, the following terms are as defined below.

Protein C refers to a vitamin K dependent serine protease with anticoagulant, anti-inflammatory, and profibrinolytic properties which includes, but is not limited to, plasma derived and recombinant produced protein C. Protein C includes and is preferably human protein C although protein C may also include other species or derivatives having protein C proteolytic, amidolytic, esterolytic, and biological (anticoagulant, pro-fibrinolytic, and anti-inflammatory) activities. Examples of protein C derivatives are described by Gerlitz, et al., U.S. Pat. No. 5,453,373, and Foster, et al., U.S. Pat. No. 5,516,650, the entire teachings of which are hereby included by reference.

Zymogen—an enzymatically inactive precursor of a proteolytic enzyme. Protein C zymogen, as used herein, refers to secreted, inactive forms, whether one chain or two chains, of protein C.

Activated protein C or aPC refers to protein C zymogen which has been converted by limited proteolysis to its activated form. aPC includes and is preferably human protein C although aPC may also include other species or derivatives having protein C proteolytic, amidolytic, esterolytic, and biological (anticoagulant or pro-fibrinolytic) activities. Examples of protein C derivatives are noted above in the description of protein C.

HPC—human protein C zymogen.

r-hPC—recombinant human protein C zymogen.

r-aPC—recombinant human activated protein C produced by activating r-hPC in vitro or by direct secretion of the activated form of protein C from procaryotic cells, eukaryotic cells, and transgenic animals or plants, including, for example, secretion from human kidney 293 cells as a zymogen then purified and activated by techniques well known to the skilled artisan and demonstrated in Yan, U.S. Pat. No. 4,981,952, and Cottingham, W097/20043, the entire teachings of which are herein incorporated by reference.

Plasma derived activated protein C—activated protein C produced by activating plasma HPC as described in Eibl, U.S. Pat. No. 5,478,558, the entire teaching of which is herein incorporated by reference.

Continuous infusion—continuing substantially uninterrupted the introduction of a solution into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Unit dosage form—refers to physically discrete units suitable as unitary dosages for human subjects, each unit containing a predetermined quantity of active material calculated to produce the desired therapeutic effect, in association with a suitable pharmaceutical excipient.

Pharmaceutically effective amount—represents an amount of a compound of the invention that is capable of inhibiting sepsis in humans. The particular dose of the compound administered according to this invention will, of course, be determined by the attending physician evaluating the particular circumstances surrounding the case.

The present invention provides for the treatment of sickle cell disease (SCD) or thalassemia with protein C. Protein C, with its anticoagulant, antiinflammatory, and profibrinolytic activities, is useful for the treatment of the hypercoagulable state or protein C deficiency that occurs in SCD or thalassemic patients.

The protein C administered according to this invention may be generated and/or isolated by any means known in the art or as described in U.S. Pat. Nos. 4,981,952, and 5,550,036, herein incorporated by reference. For example, protein C can be produced by secreting full-length, soluble protein C, or biologically active polypeptide variants of protein C from a cell which comprises (a) constructing a vector comprising DNA encoding protein C; (b) transfecting the cell with the vector; and (c) culturing the cell so transfected in culture medium under conditions such that full length soluble protein C or biologically active polypeptide variants of protein C, is secreted. Further, the cell is a eukaryotic cell, e.g. mammalian cell such as Syrian hamster AV12 cell, human embryonic 293 cell, or Baby Hamster Kidney cell.

The protein C used in the treatment of SCD or thalassemia can be formulated according to known methods to prepare pharmaceutically useful compositions. For example, a desired formulation would be one that is a stable lyophilized product of high purity comprising a bulking agent such as sucrose, a salt such as sodium chloride, a buffer such as sodium citrate and protein C or aPC.

The protein C will be administered parenterally to ensure its delivery into the bloodstream in an effective form by injecting the appropriate dose as continuous infusion for about 1 hour to about 240 hours.

Those skilled in the art can readily optimize pharmaceutically effective dosages and administration regimens for therapeutic compositions comprising protein C, as determined by good medical practice and the clinical condition of the individual patient. Generally, the amount of protein C administered will be from about 5.0 μg/kg/hr to about 250 μg/kg/hr. Preferably, the protein C used in the treatment of SCD is activated protein C (aPC). The amount of aPC administered will be from about 1.0 μg/kg/hr to about 96 μg/kg/hr. More preferably the amount of aPC administered will be about 1.0 μg/kg/hr to about 50 μg/kg/hr. While more preferably the amount of aPC administered will be about 1.0 μg/kg/hr to about 35 μg/kg/hr. Even more preferably the amount of aPC administered will be about 5.0 μg/kg/hr to about 30 μg/kg/hr. Yet even more preferably the amount of aPC administered will be about 15 μg/kg/hr to 30 μg/kg/hr. Still even more preferably the amount of aPC administered will be about 20 μg/kg/hr to 30 μg/kg/hr. The preferable amount of aPC administered will be about 24 μg/kg/hr. The most preferable amount of aPC administered will be about 48 μg/kg/hr. The appropriate dose of aPC administered will result in a reduction of the thrombotic complications associated with SCD.

The plasma ranges obtained from the amount of aPC administered will be about 2 ng/ml to about 300 ng/ml. The preferred plasma ranges are from about 2 ng/ml to 200 ng/ml. Most preferably, plasma ranges are from about 30 ng/ml to about 150 ng/ml and still more preferably about 100 ng/ml.

Alternatively, the aPC will be administered by injecting one third of the appropriate dose per hour as a bolus injection followed by the remaining two thirds of the hourly dose as continuous infusion for one hour followed by continuous infusion of the appropriate dose for twenty-three hours which results in the appropriate dose administered over 24 hours. In addition, the bolus injection will be administered via an intravenous bag drip pump or syringe pump at 2 times the normal rate for 15 minutes followed by 1.5 times the normal rate for 45 minutes. The normal rate i.e. that rate which has been determined to administer the appropriate dose level of the therapeutic agent per time period, is then continued for up to 240 hours.

The use of protein C in the treatment of SCD or thalassemia as presented in the present invention will provides a needed therapy for a potentially serious and debilitating disorder. The use of protein C is efficacious and avoids complications such as bleeding tendency, toxicity, and other general side effects of currently available anti-coagulant agents.

The following examples are provided merely to further illustrate the present invention. The scope of the invention shall not be construed as merely consisting of the following examples.

Preparation 1

Preparation of Human Protein C

Recombinant human protein C (r-hPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 7.4. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.81 or 1.85, respectively.

Preparation 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/mL resin. The thrombin solution was circulated through the column for approximately 3 hours before adding 2-amino-ethanol (MEA) to a concentration of 0.6 mL/L of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified r-hPC was made 5 mM in EDTA (to chelate any residual calcium) and diluted to a concentration of 2 mg/mL with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the r-hPC and thrombin resin. The effluent was collected and immediately assayed for amidolytic activity. If the material did not have a specific activity (amidolytic) comparable to an established standard of protein C, it was recycled over the thrombin column to activate the r-hPC to completion. This was followed by 1:1 dilution of the material with 20 mM buffer as above, with a pH of either 7.4 or 6.5 to keep the protein C at lower concentrations while it awaited the next processing step.

Removal of leached thrombin from the protein C material was accomplished by binding the protein C to an anion exchange resin (Fast Flow Q, Pharmacia) equilibrated in activation buffer (either 20 mM Tris, pH 7.4 or 20 mM Tris-acetate, pH 6.5) with 150 mM NaCl. Thrombin does not interact with the anion exchange resin under these conditions, but passes through the column into the sample application effluent. Once the protein C is loaded onto the column, a 2–6 column volume wash with 20 mM equilibration buffer is done before eluting the bound protein C with a step elution using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The anticoagulant activity of activated protein C was determined by measuring the prolongation of the clotting time in the activated partial thromboplastin time (APTT) clotting assay. A standard curve was prepared in dilution buffer (1 mg/mL radioimmunoassay grade bovine serum albumin [BSA], 20 mM Tris, pH 7.4, 150 mM NaCl, 0.02% $NaN_3$) ranging in protein C concentration from 125–1000 ng/mL, while samples were prepared at several dilutions in this concentration range. To each sample cuvette, 50 $\mu$L of cold horse plasma and 50 $\mu$L of reconstituted activated partial thromboplastin time reagent (APTT Reagent, Sigma) were added and incubated at 37° C. for 5 min. After incubation, 50 $\mu$L of the appropriate samples or standards were added to each cuvette. Dilution buffer was used in place of sample or standard to determine basal clotting time. The timer of the fibrometer (CoA Screener Hemostasis Analyzer, American Labor) was started immediately after the addition of 50 $\mu$L 37° C. 30 mM $CaCl_2$ to each sample or standard. Activated protein C concentration in samples are calculated from the linear regression equation of the standard curve. Clotting times reported here are the average of a minimum of three replicates, including standard curve samples.

The above descriptions enable one with appropriate skill in the art to prepare protein C for utilization in the treatment of sickle cell disease.

Preparation 3

Formulation of Activated Protein C

A stable lyophilized formulation of activated protein C was prepared by a process which comprises lyophilizing a solution comprising about 2.5 mg/mL activated protein C, about 15 mg/mL sucrose, about 20 mg/mL NaCl, and a sodium citrate buffer having a pH greater than 5.5 but less than 6.5. Additionally, the stable lyophilized formulation of activated protein C comprises lyophilizing a solution comprising about 5 mg/mL activated protein C, about 30 mg/mL sucrose, about 38 mg/mL NaCl, and a citrate buffer having a pH greater than 5.5 but less than 6.5.

The ratio of protein C:salt:bulking agent (w:w:w) is an important factor in a formulation suitable for the freeze drying process. The ratio varies depending on the concentration of protein C, salt selection and concentration and bulking agent selection and concentration. Particularly, a ratio of about 1 part activated protein C to about 7.6 parts salt to about 6 parts bulking agent is preferred.

A unit dosage formulation of activated protein C suitable for administration by continuous infusion was prepared by mixing activated protein C, NaCl, sucrose, and sodium citrate buffer. After mixing, 4 mL of the solution was transferred to a unit dosage receptacle and lyophilized. The unit dosage receptacle containing about 5 mg to about 20 mg of activated protein C, suitable for administering a dosage of about 0.01 mg/kg/hr to about 0.05 mg/kg/hr to patients in need thereof, was sealed and stored until use.

EXAMPLE 1

A placebo-controlled Double Blind Trial of Recombinant Human Activated Protein C (r-aPC) in Patients with Sickle Cell Disease (SCD)

Studies of sickle cell disease (SCD) patients in pain crisis have demonstrated abnormalities of platelet survival and aggregation as well as alterations in clotting factors. Vascular occlusion in the microcirculation is a key feature in the pathogenesis of homozygous SCD. The process of vaso-occlusion is multifactorial and coagulation disturbances are likely to contribute.

The current treatment approach to patients with SCD includes intravenous solutions of glucose and electrolytes, narcotic analgesics, and/or antiinflammatory agents. In more severe cases or following ischemeic stroke, exchange transfusions and bone marrow transplantation have been utilized.

This trial aims to show that the infusion of r-aPC results in a statistically significant reduction in the combined endpoint of reduced pain crisis and incidences of ischemic stroke in patients with homozygous SCD.

Inclusion criteria include patients with homozygous sickle cell disease from a study population of children and young adults. These patients are entered into the trial within 48 hours of hospital admission and in typical pain crisis.

Patients meeting the inclusion criteria for SCD are given intravenous solutions of glucose and electrolytes and narcotic analgesics. In addition, the patients receive either placebo or r-aPC for 96 hours. r-aPC is given in a dose of 24 μg/kg/hr.

The primary endpoint of the study is the reduction/elimination of pain crisis. The safety and efficacy of r-aPC is compared to placebo. The secondary endpoint of the trial is reduction/elimination of ischemic stroke associated with SCD.

We claim:

1. A method of treating a patient suffering from sickle cell disease (SCD) or thalassemia which comprises, administering to said patient about 1 μg/kg/hr to about 50 μg/kg/hr of human activated protein C.

2. The method of claim 1, wherein the human activated protein C is administered by continuous infusion for about 1 to about 240 hours.

3. A method of treating sickle cell disease or thalassemia in a patient in need thereof, which comprises administering to said patient a pharmaceutically effective amount of activated protein C such that an activated protein C plasma level of about 2 ng/ml to about 300 ng/ml is achieved.

4. The method of claim 3 wherein the activated protein C is administered in a bolus injection.

5. The method of claim 3 wherein the activated protein C is administered by continuous infusion for about 1 to about 240 hours.

6. The method of claim 3 wherein the activated protein C is administered first as a bolus then as a continuous infusion.

7. The method of claim 6 wherein one third of the activated protein C required to achieve activated protein C plasma levels in the range of about 2 ng/ml to about 300 ng/ml is administered in a bolus injection followed by continuous infusion of the remaining two thirds of the activated protein C.

* * * * *